(12) United States Patent
Johnson

(10) Patent No.: US 9,063,051 B2
(45) Date of Patent: Jun. 23, 2015

(54) INTRINSICALLY-CALIBRATED TRIBOMETER

(76) Inventor: Fred M. Johnson, Fullerton, CA (US)

( * ) Notice: Subject to any disclaimer, the term of this patent is extended or adjusted under 35 U.S.C. 154(b) by 0 days.

(21) Appl. No.: 14/007,487

(22) PCT Filed: Mar. 21, 2012

(86) PCT No.: PCT/US2012/029975
§ 371 (c)(1),
(2), (4) Date: Sep. 25, 2013

(87) PCT Pub. No.: WO2012/134917
PCT Pub. Date: Oct. 4, 2012

(65) Prior Publication Data
US 2014/0013822 A1 Jan. 16, 2014

(51) Int. Cl.
G01N 3/56 (2006.01)
G01N 19/02 (2006.01)
G01N 35/00 (2006.01)

(52) U.S. Cl.
CPC .......... G01N 19/02 (2013.01); G01N 35/00693 (2013.01)

(58) Field of Classification Search
CPC ....................................................... G01N 3/56
USPC ................... 73/9, 10, 7, 104, 105; 702/33, 34
See application file for complete search history.

(56) References Cited

U.S. PATENT DOCUMENTS

| 4,813,266 | A | * | 3/1989 | Nash .................................. 73/9 |
| 4,895,015 | A |   | 1/1990 | English |
| 5,575,232 | A | * | 11/1996 | Kato et al. .................. 114/67 A |
| 5,736,630 | A | * | 4/1998 | Welner ................................ 73/9 |
| 6,192,736 | B1 | * | 2/2001 | Clem .................................... 73/9 |
| 6,401,058 | B1 | * | 6/2002 | Akalin et al. ...................... 703/7 |
| 6,711,935 | B2 | * | 3/2004 | Hurson .............................. 73/9 |
| 7,143,855 | B2 | * | 12/2006 | Hopper ......................... 180/247 |
| 7,290,436 | B2 | * | 11/2007 | Olde Weghuis et al. ............ 73/9 |
| 7,398,669 | B2 | * | 7/2008 | Mahajan et al. .................. 73/10 |
| 7,584,646 | B2 | * | 9/2009 | Schleif et al. ....................... 73/9 |
| 8,346,455 | B2 | * | 1/2013 | Rado .............................. 701/80 |

(Continued)

OTHER PUBLICATIONS

PCT International Search Report, Jul. 13, 2012.

(Continued)

Primary Examiner — Hezron E Williams
Assistant Examiner — Hoang Nguyen
(74) Attorney, Agent, or Firm — WHGC, P.L.C.; John F. O'Rourke

(57) ABSTRACT

Intrinsically calibrating friction mensuration device has a drive unit with controllable motive member, configured to receive a controllable propulsion force, and to apply tractive force to a test piece on a surface. A force engine couples to the motive member, and applies the controllable propulsion force. The device includes a controller imposing a propulsion control signal actuating the force engine to produce the propulsion force. A force sensor is between the drive unit and the test piece, producing a force signal responsive to a sensed force between the drive unit and the test piece. The drive unit can self-propelled or stationary. A method includes applying an increasing tractive force to a test piece at rest; measuring the tractive force; identifying the maximum tractive force applied at incipient motion; identifying the transition between the resting test piece and incipient motion; determining the SCOF; continue motion and determine the DCOF.

20 Claims, 8 Drawing Sheets

(56) References Cited

U.S. PATENT DOCUMENTS

| | | |
|---|---|---|
| 2006/0130556 A1 | 6/2006 | Olde Weghuis et al. |
| 2006/0162420 A1* | 7/2006 | Pappas et al. .................. 73/9 |
| 2007/0068220 A1 | 3/2007 | Mahajan et al. |
| 2008/0060411 A1 | 3/2008 | Schleif et al. |
| 2009/0320557 A1* | 12/2009 | Sammoura et al. ............. 73/9 |
| 2011/0144875 A1* | 6/2011 | Rado .......................... 701/70 |

OTHER PUBLICATIONS

PCT Written Opinion of the International Searching Authority, Jul. 13, 2012.

* cited by examiner

INTRINSICALLY-CALIBRATED TRIBOMETER

BACKGROUND OF THE INVENTION

1. Field of the Invention

The present invention relates generally to the field of test measurement and more particularly to friction mensuration devices and most particularly to tribometers.

2. Background Art

Over one million people experience slip, trip, or fall accidents each year and approximately 17,000 die from the resultant fall injuries, second only to the number of automobile accident fatalities. These accidents are particularly serious for the elderly, who may suffer a fall injury that severely impairs their mobility, independence, and general health. These accidents can and do occur in a wide range of environments, including construction sites, private residences, playgrounds and recreational facilities, industrial settings, public and private property (e.g., sidewalks, highways/roadways, streets, parking lots, markets); public transportation facilities (airports, subways, train & bus stations) and facilities for the elderly and disabled. Hence, a great deal of attention is placed on the quality of walkway surfaces used for ambulation by pedestrians.

The criteria for walkway surface safety are determined by consensus of a panel of safety experts, based on measurements of the coefficient of static friction (SCOF) of surfaces under scrutiny. In general, physicists define the SCOF as the ratio of the maximum tangential force needed to cause a standard surface to slip divided by the force holding the surfaces in contact, herein called the normal force. A value of 0.5 for SCOF has been adopted as a threshold of safety for a walkway surface.

It is believed that the most representative measurements of a surface are taken in the field, that is, at the location of the surface to be tested. A large number of friction-measuring field devices (herein, tribometers) are used to perform friction measurements. Each type of field device employs a different effector mechanism for tribologic mensuration. Examples of tribometers include a variable incidence tribometer (VIT), a variable angle tribometer (VAT), a portable inclinable articulated strut slip tester (PIAST), and a family of articulated strut tribometers known in the art as Brunbager Mk. I slipmeter, Brunbager Mk. II slipmeter, and Brunbager Mk. III slipmeter, named after the device developer. An archetypal impact device is the "James" machine, is a bench mounted device, suitable for the laboratory and not the field. Each of the aforementioned tribometers may be characterized as an "impact"-type device, in which the parameter measured results from an impact between a test surface and a material sample affixed to the particular tribometer. Similar devices, such as the Sigler Pendulum or the British Pendulum, employ principles of the Conservation of Momentum to measure the kinetic forces corresponding to pendulum motion being arrested by a test material.

Each type of impact device is operator dependent, that is, the criteria for the critical onset of motion during testing cannot be uniquely determined. In addition, the "impact" aspect of these devices implies that a kinetic phenomenon is being used to determine a static phenomenon, namely the static coefficient of friction. Application of the First Law of Thermodynamics to the mechanics of impact devices shows that these devices dissipate some amount of kinetic energy during mensuration, causing wide variability in the measured value of "static" friction. Thus, a measurement reported by an impact-type device is an estimated proxy measurement for the static frictional force and, by extension, for SCOF. Not unsurprisingly, impact tribometers tend to generate non-reproducible, divergent numerical values for the same surface and condition under test. In fact, "impact devices" that rely on gravity, on spring loaded pressure, or on pneumatic pressure are actually energy converters that tend not to reliably produce their theoretically expected horizontal and vertical force components. In addition to the impact-type tribometer, a "pull"-type tribometer also is in use. Two devices exemplary of this type are known to ones of ordinary skill in the art as a horizontal pull slipmeter, and a horizontal dynamometer pullmeter. Each device relies on an operator applying a horizontal force on the slipmeter test device, which is coupled to the test sample. The point of motion initiation being taken as corresponding to the SCOF. Some "slipmeters" are closer in physical characteristics to spring-loaded fishing or laboratory scales. Again, an operator applies a horizontal force and notes the point motion begins. Variations induced by the operator are inevitable. The subjective and objective variability of device operation, unintentional or unavoidable application of non-horizontal force, and vagaries in result interpretation, can lead to a myriad of results for the same test conditions. Moreover, each of the "pull"-type devices use a respective test material (neolite, neoprene/rubber) that is generally unrepresentative of materials used by an actual pedestrian. A difficulty in reported and published measurements derived from impact and pull devices alike is that the devices produce divergent numerical values for their output. In 2005, testimony at an OSHA hearing revealed there was no test procedure or instrument that accurately correlates to the actual human walking and working condition. Thereafter, ASTM International (formerly, American Society for Testing and Materials) withdrew International Certification for all field measurement protocols for Coefficient of Friction, with no replacements. Hence, there is a need for a tribometer that provides a direct measurement for static friction force, which is operator-independent, and which produces results that are reliable, reproducible, and verifiable.

SUMMARY

Embodiments herein provide friction mensuration apparatus and methods for friction mensuration. The friction mensuration device includes a drive unit having at least one controllable motive member coupled to the drive unit, configured to receive a controllable propulsion force, and configured to apply tractive force to a test piece on a surface responsive to the controllable propulsion force. The device also includes a force engine coupled to the at least one controllable motive member, and configured to apply the controllable propulsion force to the at least one controllable motive member. In addition, the device includes a controller coupled to the force engine, and imposing a propulsion control signal to the force engine, in which the propulsion control signal is actuating the force engine to produce the controllable propulsion force. Furthermore, the device includes a force sensor coupled between the drive unit and the test piece, the force sensor producing a force signal responsive to a sensed force between the drive unit and the test piece. In the device, the drive unit is intrinsically calibrated. The friction mensuration device of Claim 1, wherein the drive unit is a self-propelled drive unit coupled to the test piece. In some embodiments the drive unit is a stationary drive unit coupled to the test piece. In other embodiments the drive unit is a self-propelled drive unit coupled to the test piece.

An embodiment of the apparatus includes the test piece having a preselected test material thereon, wherein the test piece is oriented to place the preselected test material in contact with a test surface, and wherein the test piece receives the tractive force. The sample carrier translates the tractive force into a test force applied to the preselected material sample, and the test force applied to the preselected material sample is representative of a friction force between the preselected material sample and the surface. The sensed force can be a static friction force, or a dynamic friction force.

In another embodiment, the device, in response to a received force signal, the controller actuates the force engine to produce a controllable propulsion force on the at least one controllable motive member and, responsive thereto, imposes a friction force imposed between the test surface and the preselected sample material. In yet another embodiment, the friction mensuration device further includes a mensuration memory coupled to the controller and having memory storage units. The mensuration memory is configured to receive from the controller a plurality of representations of the sense force, and to retain respective ones of the plurality of representations of the sense force. In still other embodiments, the test piece is a contact sled further including a carrier having facets. Each of the facets includes a sample carrier thereon, with each sample carrier being disposed to releasably retain a respective preselected material sample. The carrier can be disposed to position one of the preselected test materials in contact with the surface.

In other embodiments of the friction mensuration device, the force engine applies the tractive force during a first portion of a test epoch, corresponding to the static coefficient of friction. In still another embodiment of the device, one of the preselected sample materials is a control sample material. In yet other embodiments, the control sample material is a piece of footwear or is a resin rubber constituent of a preselected rubber soling material.

An embodiment of a method of friction mensuration, includes applying an increasing tractive force to a test piece at rest on a test surface at the beginning of a test epoch; measuring the tractive force on the test piece at rest on a test surface during the test epoch; identifying the maximum tractive force applied at incipient motion of the test piece on the test surface during the test epoch; identifying a nonce of the test epoch signifying the transition between the test piece at rest and incipient motion; determining the static coefficient of friction of the test piece relative to the test surface for the test epoch; and measuring the tractive force used to continue motion in the test sled for the test epoch. The test period can be created from a plurality of sequential test epochs. In a method embodiment of friction mensuration the test piece is stopped between selected test epochs in the test period.

In other embodiments of the method above can be included applying tractive force to the test piece during a calibration period; suspending the test piece separated from the test surface during the calibration period; and weighing the suspended test piece, wherein the weighing is a constituent of intrinsically calibrating a friction mensuration device. In yet other embodiments, the method further includes continuing the tractive force during the test epoch; stopping the tractive force at the end of a test epoch; determining the static coefficient of friction of the test piece relative to the test surface; and determining the dynamic coefficient of friction of the test piece relative to the test surface. The method can be for a intrinsically calibrated device, which method includes applying tractive force to the test piece during a calibration period; suspending the test piece separated from the test surface during the calibration period; and weighing the suspended test piece, wherein the weighing is a constituent of intrinsically calibrating a friction mensuration device.

BRIEF DESCRIPTION OF THE DRAWINGS

The figures herein provide illustrations of various features and embodiments in which.

Figure 1A:
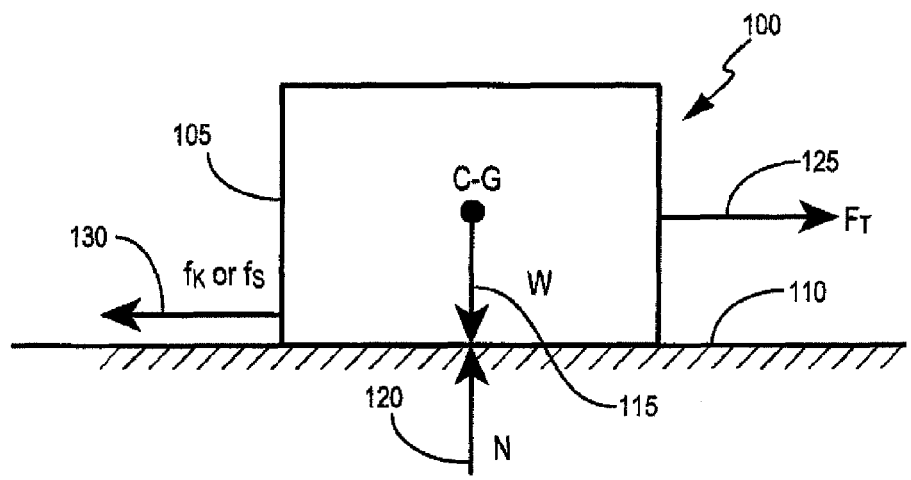
FIG. 1A is an illustration of a model of tractive, frictional, gravitational, and normal forces used to effect the embodiments of the present invention.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated.

DETAILED DESCRIPTION OF THE INVENTION

Figure 1B:
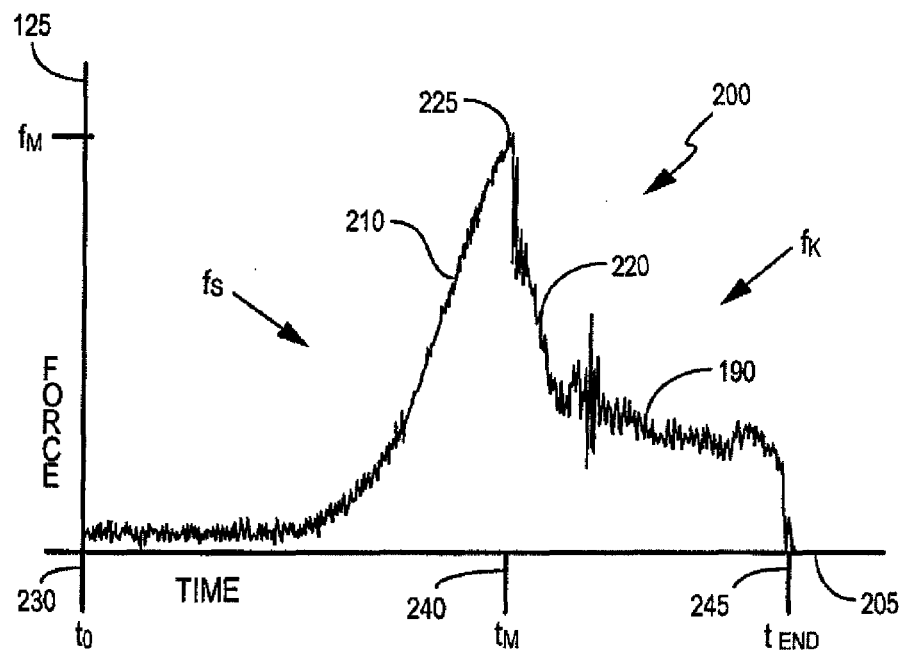
FIG. 1B is an illustration of static and dynamic forces arising from the model in FIG. 1A.

FIGS. 1A and 1B are physical and frictional models, respectively, which illustrate the principles of the embodiments described herein. FIG. 1A depicts a physical model 100 having two elements 105, 110 in frictional contact. In general, model 100 can be illustrated with a surface of first element 105 being disposed second element 110. First element 105 may be a test material. Second element 110 may be a test surface. Second surface 110 is depicted as being substantially horizontal, relative to gravitational force G (115). On a terrestrial surface (e.g., an x, y plane in an x, y, z space), first element 105 experiences normal force N 120 opposing gravitational force G 115. In general, normal force N 120 is produced at a right angle (∟ 90°) to the mutual interface between first element 105 and second element 110, that is, where the opposing surfaces of first element 105 and second element 110 meet. When tangential force F 125, which is depicted as substantially horizontal, is gradually applied to first element 105, relative to second element 110, element 105 tends to remain at rest. Force F 125 is resisted by opposing frictional force f 130. As force F 125 increases to a maximum value, relative motion will occur between first element 105 and second element 110. That is, first element 105 will begin to slide over second element 110. The maximum value of frictional force f 130, at the point of movement, corresponds to a value for the coefficient of static friction (SCOF). Typically, a decreased tangential force F 125 may be used to sustain the relative movement, once the critical value of measured force F is reached.

FIG. 1B illustrates a friction model 200, which can be represented within the context of physical model 100 in FIG. 1A, as measured by tangential force F 125, applied as a function of time t 205. Friction force can be manifest in two forms: (1) static friction, $f_S$ 210 and (2) kinetic friction, $f_K$ 220. In general, the laws of friction are empirical in character and approximate in their predictions. Two basic empirical laws of friction can be expressed as: (1) the static friction is approximately independent of the area of contact over wide limits; and (2) the static frictional force is proportional to the normal force N (e.g., force N 120). Typically, static friction force $f_S$ 210 can be associated with the force F 125 applied to at-rest first element 105 in contact with second element 110. As illustrated in FIG. 1B, the period during which this force F 125 is applied, and frictional force f resists in the form of static friction force $f_S$ 210, extends from the initial application of force F 125 at time $t_0$ 230 to the time at which applied force F 125 coincides with the initiation of motion in first element 105 at time $t_M$ 240. At time nonce $t_M$ 240, contact is broken between opposing surfaces of first element 105 and second element 110, allowing first element 105 to move relative to second element 110. In this context, such movement is called "sliding." This point of maximum value establishes the value of $f_M$ 225, whose magnitude defines one of the components for determining the SCOF. Once sliding occurs, a smaller, kinetic, force, generally indicated by $f_K$ 220, is needed to maintain motion of the first element 105 in contact with second element 110. The period during which this force F 125 is applied, and frictional force f resists, in the form of kinetic friction force $f_K$ 220 extends from the initial movement of first element 105 at time $t_M$ 240 until the force F 125 is no longer measured, represented by time $t_{END}$ 245. Often, dynamic forces and surface characteristics can provide greater or lesser resistance, as illustrated by oscillations 190 in $f_K$ 220.

The empirical relationship between the magnitudes of the normal component N 120 and the static frictional force $f_M$ 225 at time $t_M$ 240, may be characterized by:

$$f_M = \mu_S \times N \quad \text{(EQ. 1)}$$

where $f_M$ 185 corresponds to the value for static friction force $f_S$ 160 at the moment of motion, $t_M$ 175, $\mu_S$ corresponds to the coefficient of static friction (SCOF), and N 120 corresponds to the normal force at the mutual interface of elements 105 and 110. As understood by those of ordinary skill in the art, an accurate and reliable measurement of $f_M$ 185 can directly produce a SCOF with similar characteristics, whereas friction measurements derived from dynamic processes may deliver unreliable, irreproducible, and divergent results.

In embodiments of the present invention, force F 125 can be gradually applied in a uniformly or monotonically, increasing manner, the transition between $f_S$ 160 and $f_K$ 165 can be readily detected, allowing direct measurement of maximum static force $f_M$ 185. An event during which frictive force is measured is hereinafter designated as a "test," although parameters other than friction force may be measured during a test.

For the purposes of the present description, the period of time between the test initiation, $t_0$ 170 and test completion, $t_{END}$, 180, will hereinafter be designated a "test epoch," or simply, an "epoch." Embodiments in accordance with the present invention can be configured to perform tests and to collect information, including frictional force data, during one or more test epochs.

Figure 2:
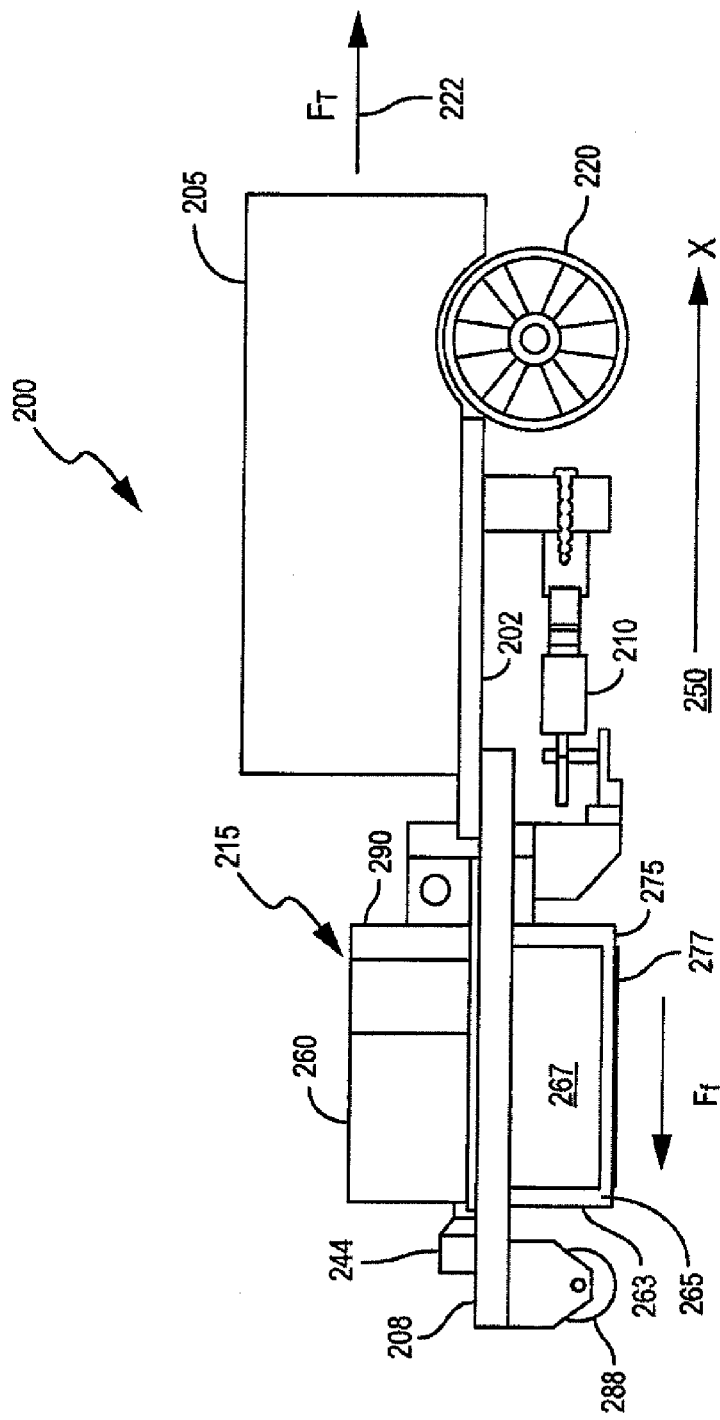
FIG. 2 is a side view illustration of one embodiment of an self-propelled intrinsically calibrated tribometer, in accordance with the teachings of the present invention.
Figure 3:
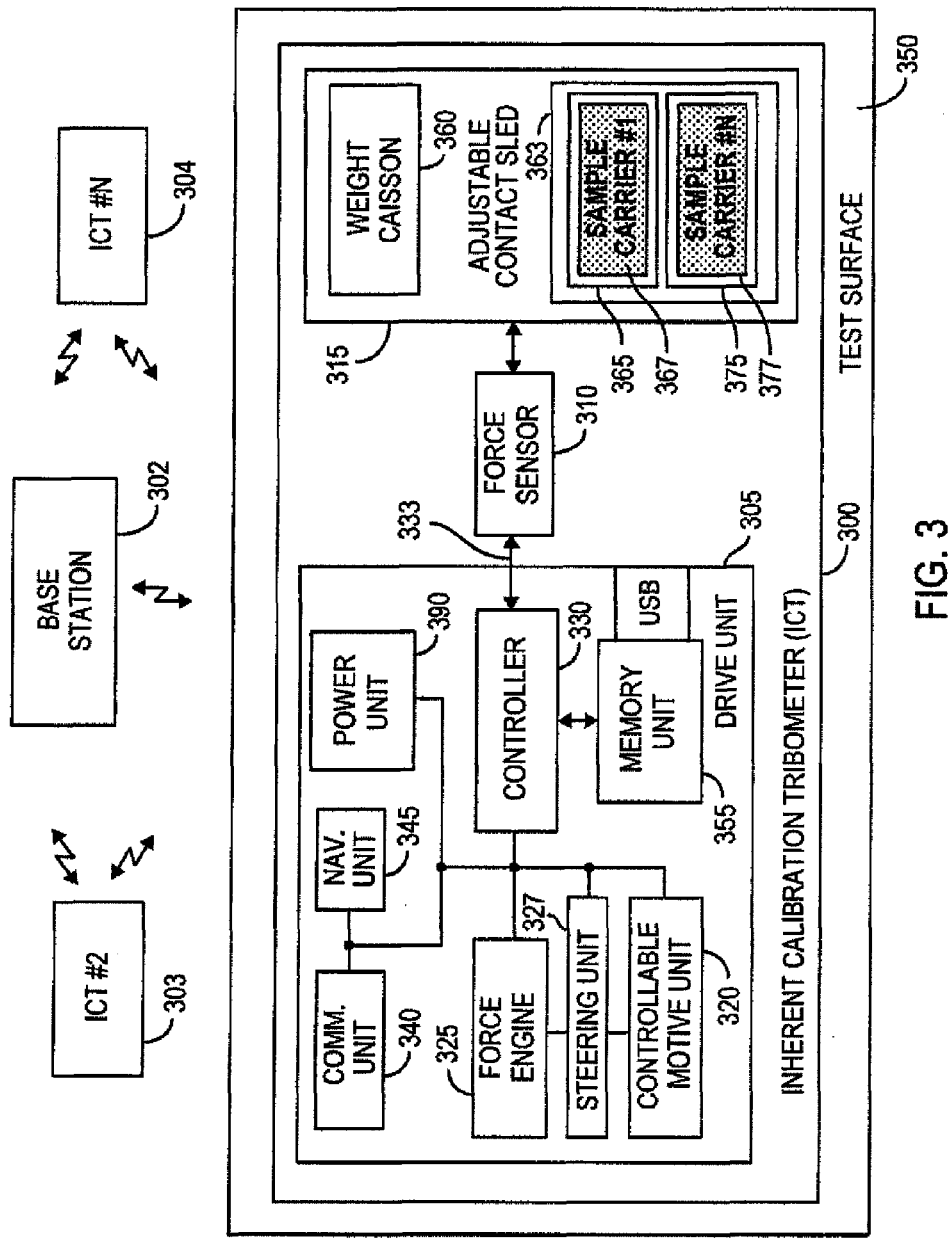
FIG. 3 is a block diagram model of an embodiment of an intrinsically calibrated tribometer, in accordance with the teachings of the present invention.

FIG. 2 illustrates a side view of an embodiment of a self-propelled embodiment of an intrinsically calibrated tribometer generally at 200, which can include functional units described in FIG. 3, with respect to tribometer 300. Tribometer 200 is depicted in an example configuration, to illustrate features of certain self-propelled embodiments described herein. Tribometer 200 can include drive unit 205, contact sled 215, and force sensor 210 coupled between drive unit 205 and contact sled 215. Tribometer may be self propelled by at least one controllable motive member 220 attached to the frame of drive unit 205, and configured to receive a controllable propulsion force $F_T$ 222 from force engine 225 (not shown but typically within a case of drive unit 205). Force $F_T$ causes tribometer 200 to be propelled in a selected direction (e.g., X direction) on test surface 250. Drive unit 205 may include one or more guide rails 202, which may include one or more followers 208. Followers 208 generally support contact sled 215 and assist rails 202 convey tractive force to sled 215. Guide rails 202 can be configured to slidingly support contact sled 215 relative to drive unit 205. Wheels 288 typically do not come into contact with test surface 250 during operation but may be used to easily move tribometer 200 in a manner similar to a wheeled luggage carrier.

Embodiments of tribometer 200, relative to FIG. 1A, are configured to contribute minimally, if at all, to the normal reactive force N, which acts in opposition to the gravitationally-induced weight force W. Contact sled 215 can be disposed with slotted support frame 208, which may slidingly engage guide rails 202.

Intrinsically calibrated tribometer 200 can include a weight caisson 260 in contact sled 215. Weights, such as sand- or lead-filled stockinette material can be disposed in caisson 260. Also caisson may be used in conjunction with stanchion 275 which may be used to receive calibrated weights, e.g., weight 290, to create a preselected sled weight for caisson 260 and, by extension, sled 215. Sled 215 can include a faceted sample carrier 263 between caisson 260 and test surface 250. Each facet 265, 275, of carrier 263 can be configured to retain thereon a respective predetermined test sample 267, 277 for frictional testing with test surface 250. In FIG. 2, test sample 277 is depicted to be in flat, parallel contact with test surface 250.

Turning to FIG. 3, a block diagram illustrating an embodiment of the present invention is shown. Intrinsically calibrated tribometer 300 can include drive unit 305, force sensor 310 and contact sled 315. Tribometer 300 can be disposed on preselected test surface 350. In certain embodiments, drive unit 305 is provided for self-propulsion of tribometer 300. Self-propulsion can be achieved by coupling drive unit 305 to at least one controllable motive member 320, which can be configured to propel drive unit 305 on test surface 350. For example, controllable motive member 320 may be, without limitation, a wheel, a tread, a ball, a roller, a drum, a coil, or a belt. Controllable motive member 320 also may be an element configured to translate propulsive force into horizontal movement of tribometer 300, including, without limitation, a leg/pedal-type element, a crawler-type element, a peristaltic-type element, or a helical-type element.

Controllable motive member 320 can be integral with drive unit 305, or may be articulated, for example, by way of an axle, a spool, a spindle, a joint, a pendant, or a gearbox. At least one controllable motive member 320 is configured to convert a received propulsive force into motion. It is desirable that at least one controllable motive member 320 be configured to propel drive unit 305, and by extension, intrinsically calibrated tribometer 300, smoothly to minimize irregularities in forces transmitted mechanically through tribometer 300, and to provide substantially uniform propulsion.

Drive unit 305 can include force engine 325 coupled to the at least one controllable motive member 320. Force engine 325 is configured to apply a controllable propulsion force to at least one controllable motive member 320, causing tribometer 300 to be propelled in a selected direction on test surface 302. Force engine 325 may incorporate a steering unit configured to directionally manipulate the at least one controllable motive member 320, causing drive unit 305 to change the direction of propulsion. Force engine 325 may be, without limitation, a rotating electric motor, which may be operated by 12V DC power. An example of such a motor may be a 12 VDC REVERSIBLE GEARED MOTOR, such as Model CRA203 (P/N 30570) from Cramer Co., South Windsor, Conn. USA. Of course, force engine 325 may be another suitable motor such as, without limitation, be a stepper motor, a linear DC motor, a brushed DC motor, a brushless DC motor, a piezoelectric motor, or other 5 VDC to 24 VDC motor configured to produce linear self-propulsion of tribometer 300 from power unit 390, whether directly or in conjunction with mechanical motion translation elements, which may be disposed in one or both of force engine 325 or controllable motive member 320. Force engine 325 may be coupled to force sensor 310 by a screw transmission, to permit movement by infinitesimal, and nearly infinite, measures, allowing for an exceptional degree of precision currently unknown to the tribometer art.

Drive unit 305 also can include controller 330 coupled to force engine 325 and configured to impose control signal 355 on force engine 325. Control signal 355 actuates force engine 325 to produce the controllable propulsion force, F 125 from FIGS. 1-2. Typically, force engine 325 produces the controllable propulsion force F 125 in a gradual, uniformly increasing manner 160, as illustrated in FIG. 2, responsive to control signal 355 from controller 330. Controller 330 captures a high-fidelity value of peak friction force $f_M$ 185 at nonce $t_M$ 175, that is, when contact sled 315 begins to move, relative to test surface 350. Peak friction force value $f_M$ 185 can be used to determine SCOF (see EQ. 1). A frictional force signal 333 received from force sensor 310 can be sampled, for example, at a rate of about 5 samples per second to about 100 samples per second for a period of time during which peak friction force value $f_M$ 185 occurs. Sample values of frictional force 333 can be stored in a memory, such as memory 355.

Controller 330 can be a microprocessor, a microcontroller, or a state machine. An example of a suitable controller 330 includes, without limitation, a low-power, CMOS AT90USB64 8-bit microcontroller manufactured by Atmel Corporation, San Jose, Calif. USA. Controller 330 may be an integrated controller, or may be representative of a distributed cooperative of interoperating control elements disposed in drive unit 305. Controller 330 can perform a "Power On Self-Test" (POST) to verify that elements are disposed in a proper power state (ON/OFF), that tribometer 300 is configured to perform a preselected tribometric test in accordance with a predetermined tribometric process, and that sensing and mensuration elements appear operational. In addition, controller 330 can communicate "INITIATE" and "STANDBY" commands to sensing and mensuration elements to place the elements in a known initial state, and to make ready tribometer 300 for a test procedure.

Memory 355 may be coupled to controller 330, or may be integrated therein. Memory 355 may be used to store command, control, and communication information and code, which may facilitate semi-autonomous operation of tribometer 300. Memory 355 also may be used to collect data from force sensor 310 during one or more testing periods. An example of suitable memory 355 can be 2 GB×8 NAND Flash Memory model MT29F2G08 manufactured by Micron Technology, Inc., Boise, Id., USA. In addition, memory unit 355 also may be representative of one of the ubiquitous removable memory devices (e.g., "stick," "card," "pen drive"), typically using non-volatile FLASH memory technology, on which command, control, and sensed information may be at least temporarily stored. Alternately, memory unit 355 can be configured to transfer stored information to such a removable memory device in the usual course of operations, for example, autonomously, or upon command for such a transfer by base station 311.

Controller 330 can be configured to actuate intrinsically calibrated tribometer 300 to perform one test during a test epoch $t_0$ to $t_M$ (170, 180), or to perform multiple tests during respective test epochs. A testing period may contain one or more test epochs. Actuation of tribometer 300 may be performed by remote communication with controller 330, for example, from base station 302. Intrinsically calibrated tribometer 300 also can be actuated by controller 330 in response to an applied signal or environmental condition or by a signal from navigation unit 345. Controller 330 can store values corresponding to preselected test parameters, for example, in a memory within controller 330, in memory 355, which is coupled within drive unit 305 to controller 330, or to a discrete memory device, such as a USB memory "stick" which can be physically coupled to drive unit 305 and electrically coupled to controller 330 by way of communication unit 385.

Furthermore, controller 330 can be configured with well-known routines to determine for each test epoch or test period, a maximum measured friction force, a corresponding SCOF for a test epoch or test period, a corresponding DCOF for an epoch or a test period, a time, a date, location indicia, an acceleration in one or more dimensions, an ambient temperature, an ambient humidity, a pitch, a yaw, a forward or a lateral acceleration or a characterization of a physical characteristic. Acceleration, pitch, yaw, attitude, and absolute or relative position information (represented as location indicia) may be obtained by controller 330 from navigation unit 345. Also, controller 330 may be configured to calculate statistical values corresponding to aforementioned data collected from selected testing epochs including, without limitation, calculating, an average value of $f_M$, an average value of SCOF, average deviation, standard deviation, probable error, average error, force skewness or kurtosis, as well as test surface temperature, planarity, tilt, and surface and finish characteristics. Such data and the information that results therefrom can confirm accuracy, reproducibility, and reliability of tribometer 300 obtained data over multiple tests, and can assist in analyzing the preselected sample material, analyzing the preselected test surface, or both, or in characterizing variability in data which may arise under particular circumstances. Controller 330 also may be configured to record date and time for each test data set, relative or absolute location or elevation, or measurement count.

In some selected embodiments, drive unit 305 can be supplied with a communication unit 340. Communication unit 340 can be configured with at least one of a wired communication port, a wireless communication port, a memory device port, or a display port. Incoming signals to communication unit 340 may include, without limitation, commands, identifiers, and data. Outbound signals from communication unit 340 may include, without limitation, a force measurement value, a sensed environmental condition value, computed values, tribometer position, velocity, or acceleration, position, energy store level, or mesh unit synchronization.

A wired communication port can be, without limitation, a Universal Serial Bus (USB) port, IEEE 1394 serial bus port, an RS-232 serial bus port, an RS-422 serial bus port, or an unshielded twisted pair (UTP) serial port having an RJ-11 connector. Communication unit 340 may have one or more than one of such communication ports, which can be coupled to controller 330. The Atmel AT90USB64 8-bit microcontroller incorporates, for example, Universal Serial Bus (USB) On-the-Go functionality to provide bidirectional wired communication between tribometer 300 and a base station 302. Wireless communication between tribometer 300 and base station 302 may be implemented in tribometer 300, base station 302, or both, for example, using an USB adapter (or USB dongle), coupled to, or integrated in communication unit 385. In one non-limiting alternate example, a DWA-210 Xtreme N® Duo USB Adapter (dongle) available from D-Link Systems, Inc., Fountain Valley, Calif., USA may be used. The DWA-210 wireless dongle provides wireless IEEE 802.11a/b/g/n WLAN capability via a bidirectional USB link. Alternately, and without limitation, a WPAN wireless link may be used. For example, DBT-120 Wireless BLUETOOTH® 2.0 USB Adapter (dongle), also from D-Link Systems, Inc., may implement IEEE 802.15.2/BLUETOOTH® functionality. Also, a WPAN implementation may use an @ANY2400 IEEE 802.15.4/ZigBee™ USB Dongle, from Adaptable Network Solutions GmbH, Dresden, Del. The well-known IEEE 802.15.4 standards, or the ZigBee™ specifications, may exemplify techniques for supporting a point-to-point bidirectional link, between base 302 and tribometer 300. However, an IEEE 802.15.4 standard, or the ZigBee™ specifications, also may provide a technique by which to implement a cooperative or mesh network or other distributed, intelligent interaction between or among multiple ones 303, 304 of tribometer 300. The aforementioned dongle providers, and their vendors, also make available tutorial matter and software, by which such dongles may be controlled. At least a portion of the software provided for a respective dongle may be programmed into memory unit 355. In yet another alternative embodiment, communication unit 385 may be communicatively coupled to base station 302 by a wireless transceiver different from a USB connection. For example, communication unit 385 may be configured with an electromagnetic communication transceiver, using electromagnetic radiation in the established RF signal ranges, or in the established infrared signal ranges. Acoustic or ultrasonic communication may be effected by communication unit 385. One of ordinary skill in the art could substitute other configurations and processors to provide similar functionality, in light of the teachings herein.

Controller 330 also may be coupled to navigation unit 345 disposed in tribometer 300. Navigation unit 345 may be used to determine a location of tribometer 300, geospatially, relative to base station 302, or both. In the present context, "determine" can mean to cause tribometer 300 to be propelled to a preselected location, within a predetermined frame of spatial reference (add XYZ to FIG. 3); to resolve the location of tribometer 300, within the predetermined frame of spatial reference; or both. Navigation unit 345 can include, for example, an accelerometer, an inertial navigation unit, a global positioning system (GPS) unit, or a combination of an accelerometer and an inertial navigation unit, or an accelerometer and a global positioning system (GPS) unit, an accelerometer and an inertial navigation unit, or an inertial navigation unit and a global positioning system (GPS) unit. An accelerometer may be a 1-axis accelerometer, a 2-axis accelerometer, or a 3-axis accelerometer. By increasing the number of axes along which measurements were taken, an accelerometer in the context of the present invention, navigation unit 345 can provide increasing functionality including sensing one or more of acceleration (translational) data, tilt data, shock data or vibration data. An inertial measurement unit (IMU) may be a 4-degrees-of-freedom (DoF), or a 6-DoF inertial measurement unit. By increasing the degrees of freedom in an inertial navigational unit in the context of the present invention, navigation unit 345 can provide increasing functionality including one or more of sensing acceleration data, vibration data, rotation data, tilt data, shock data, and multiple degrees-of-freedom motion data. Such data may facilitate a pre-test calibration of tribometer 300, an in-test or a post-test correction of a position, a force, or a friction measurement by tribometer 300, or in-test correction of propulsion direction. Navigation unit 345, if disposed in the multiple ones 300, 303, or 304, can facilitate purposeful coordinated mensuration of larger areas, for example, simultaneously. Navigation units may be configured with a cooperative inertial navigation module, or a GPS navigation module, or a custom navigation module, to facilitate precise placement and movement of one or more of intrinsically calibrated tribometers 300, 303, 304. Navigation may be initiated or controlled by base station 302, or it may be initiated or controlled locally, for example, on tribometer 300, and reported to base station 302.

Non-limiting examples of an accelerometer can be an ADXL-103 accelerometer (1-axis), an ADXL-203 or an ADIS-210003 accelerometer (2-axis), or an ADXL-327 accelerometer (3-axis), each from Analog Devices, Inc., Norwood, Mass. USA. Non-limiting examples of an inertial measurement unit can be an ADIS-16300 (4-DoF) or an ADIS-16360 IMU (6-DOF), with each IMU also being produced by Analog Devices, Inc. A non-limiting example of a GPS unit can be an STA2058 TESEO™ GPS platform IC, manufactured by STMicroelectronics, Geneva, CH. Of course, an artisan of ordinary skill could substitute other motion detection elements without departing from the scope of the invention herein.

Contact sled 315 can be coupled to drive unit 305 so that contact sled 315 receives at least a portion of the controllable propulsion force, and is drawn in the direction of drive unit 305. Contact sled 315 can be configured to have a test sample carrier 360 disposed thereon, which is configured to releasably retain preselected material sample 365. Preselected material sample 365 can be a material to be tested for slip or wear resistance, slipperiness, or other physical characteristic, when applied frictively to a test surface (not shown). Contact sled 315 can be formed with a predetermined mass which, under gravitational acceleration, will impart to contact sled 315 a predetermined weight. However, some types of friction mensuration may call for contact sled 315 to have a greater mass or weight. To this end, some embodiments of tribometer 300 include weight caisson 360, which can be a shaped framework or container in which one or more slugs, each having a preselected slug weight, may be disposed in weight caisson to alter, typically increase, the predetermined weight of contact sled 315. Alternatively, weight caisson 360 may be disposed in drive unit 305, or in both contact sled 315 and drive unit 305, in accordance with a balanced weight distribution of tribometer 300. In general, contact sled 315 orients sample carrier 363 to place preselected test material in carrier 365 in contact with the surface 350. Contact sled 315 conveys the propulsion force to sample carrier 360 which, in turn, translates the at least a portion of the propulsion force into a test force applied to the preselected material sample 365. Upon initiation of motion of preselected material sample 365, relative to test surface (not shown), the test force applied to the preselected material sample is representative of a friction force between the preselected material sample and the test surface. The test force corresponds to F 125 in FIG. 1, and the friction force corresponds to force $f_M$ 185, in FIG. 2.

In selected embodiments of tribometer 300, contact sled 315 may be disposed with a carrier having facets 365, 375, with each facet 365, 375 being disposed to releasably retain a respective preselected material sample thereon. A multifaceted carrier 363 facilitates seriatim tribometry of multiple material samples. For example, first preselected material sample in carrier facet 365 may be used to determine a first SCOF of a dry, clean preselected test surface and, thereafter, second preselected material sample in carrier facet 375 may be used to determine a second SCOF after the preselected test surface has been wetted, contaminated, or both. In other embodiments of tribometer 300, contact sled 315, itself, may be configured with facets. In one non-limiting example, tribometer 300 may employ a contact sled 315, having a hexagonally-shaped cross-section and six longitudinally-oriented facet surfaces, with each disposed with a respective sample carrier 365, 375. As with other embodiments, each respective sample carrier 365, 375 can be disposed to releasably retain a respective preselected material sample 367, 377.

Force sensor 310 couples drive unit 305 to contact sled 315. As drive unit 305 is propelled, tension is applied to force sensor 310, in the course of transmitting the propulsion force to contact sled 315. Force sensor 310 can be configured to sense a tensional force which may develop between drive unit 305 and contact sled 315, which tensional force is representative of at least a portion of the propulsion force. Force sensor 310 can be, without limitation, a load cell, or a strain sensor, configured to measure loads of between about 0.05 lbf to about 20 lbf, and typically, between about 0.1 lbf to about 10 lbf. One example of a load cell or strain sensor can be a 20-lb rated thin beam load cell, P/N TBS-20 made by Transducer Techniques, Inc., Temecula, Calif., USA, although other load cells or strain sensors may be used. Force sensor 310 can generate force signal 355, and impose force signal 355 on controller 330. In general, force signal 355 can be representative of a horizontal friction force created by an interface between test surface and a test sample in reaction to gravitational forces, W 115, a normal force, such as N 120, and propulsive force F 125 in FIG. 1. Typically, force signal 355, when generated by force sensor 310 and imposed on controller 330, can cause controller 330 to actuate force engine 325 to controllably apply a motive force to controllable motive unit 335.

Base station 302 can be communicatively coupled with tribometer 300, for example, by a wired link, a wireless link, or both. Base station 302 may be used to transmit commands to, and to receive data from tribometer 300. Base station 302 may be a handheld system or smaller, or it may be a laptop computer, a desktop computer, or an industrial controller configured to communicate with at least one tribometer. In some in-the-field environments, a ruggedized handheld computer 302 may communicate with tribometer. Base station 302 also may be a notebook, or a laptop, or another computing device capable of bidirectional communication with tribometer 300, and having an operator interface to enter data, to perceive information, or both. A wired link can be a USB connection, a IEEE Std. 1394 connection, an RS-232 connection, an RS-422 connection, an unshielded twisted pair (UTP) connection, or a Controller-area network (CAN) connection. A wireless link can be a USB On-the-Go™ wireless link, an IEEE Std. 802.11 a/b/g/n link, an IEEE Std. 802.15 link (personal area network), or any other suitable non-interfering ISM-type wireless link. Base station 302 can be used to set a value of at least one preselected parameter used to control operation of tribometer 300, for example, rate of controllable propulsion force application, sampling rate for sensed force values from force sensor 310, or the number or type of sensed force, speed, temperature, humidity, or other sensed data collected from tribometer 300.

Base station 302 is used to initiate self-propulsion, for example, by transmitting a "BEGIN TEST" signal to tribometer 300, or by other well-known signal techniques, using an established communication link, thereby removing idiosyncratic, irreproducible variations in force magnitude and direction, applied by a human test device operator to a test material relative to a test surface. Tribometer 300 is configured to produce results that are both accurate and reproducible from test to comparable test, thereby allowing substantially direct measurement of frictional forces between a preselected test material and a preselected test surface, and computation of $\mu_S$. Consequently, the reckoning of SCOF, in accordance with the application of the present invention, produces SCOF values grounded in actual values of static friction, and not derived or confounded by kinetic processes. Approximately 20 to about 30 automatic force readings may be taken, stored in memory, and displayed during each test epoch, although more or fewer samples may be taken.

In alternative embodiments, drive unit 305 is configured to be a stationary base 305, in which navigation unit 345 or steering unit 327 may not be used. Also, controllable motive unit 320 may be configured to draw a cord (not shown), such as by a pulley urged by force engine 325. Force sensor 310 also may be configured to sense force delivered to adjustable test sled 315 by controllable motive unit 320, by force engine 325, or by both unit 320 and engine 325. Test sled 315 can be configured as a weighted box with up to four (4) to six (6) facets, or sides, with a facet being configured to receive a predetermined material sample. A predetermined weight, such as 5 lbm can be a weight caisson secured in a closed box of test sled 315 by an epoxy resin adhesive, to prevent weight movement. Thus, alternative embodiments of an intrinsically calibrated tribometer 300 may include those that are configured with a stationary base 305, as well as those which are non-stationary, for example the aforementioned self-propelled drive unit 305. In the alternatives, test sled 315 receives an applied tractive force from which static or dynamic friction forces and corresponding static or dynamic coefficients of friction may be measured. Furthermore, in the alternatives, a weighted shoe may be used in place of adjustable contact sled 315, so that frictional parameters of an actual shoe may be measured. Unlike some prior tribometers, the test piece, e.g. contact sled, test sled, or shoe 315, is not slammed against the test surface, inducing error by creating a vacuum between the test piece and the test surface, and by oscillations which may be introduced into a force measurement.

Tests, self-calibrations and measurements performed by the embodiments of intrinsically calibrated tribometer 300 can be reproducible and operator independent, unlike the current state of the tribometer art. Moreover, tribometer 300 can be intrinsically calibrated using a known test object 315, which may be, without limitation, a contact sled, a test sled, or another test object such as a shoe. Intrinsic calibration can be performed by providing a gantry rising upwards over tribometer unit 305 and having a pulley at the apex. Known test object 315 may be attached to force sensor 310 using a strong, substantially non-elastic cord and force engine 325 may apply tractive force, causing known test object to be suspended off of the base resting surface. Once suspended, measurements of known test object weight 315 may be taken, and used to intrinsically calibrate tribometer 300. The intrinsic calibration is operator-independent. Intrinsic calibration using a test object can lead to reliable, reproducible, and verifiable determination of coefficient of friction for each test epoch or period. This intrinsic calibration configuration and technique also are not known in the current tribometer art.

Figure 4:
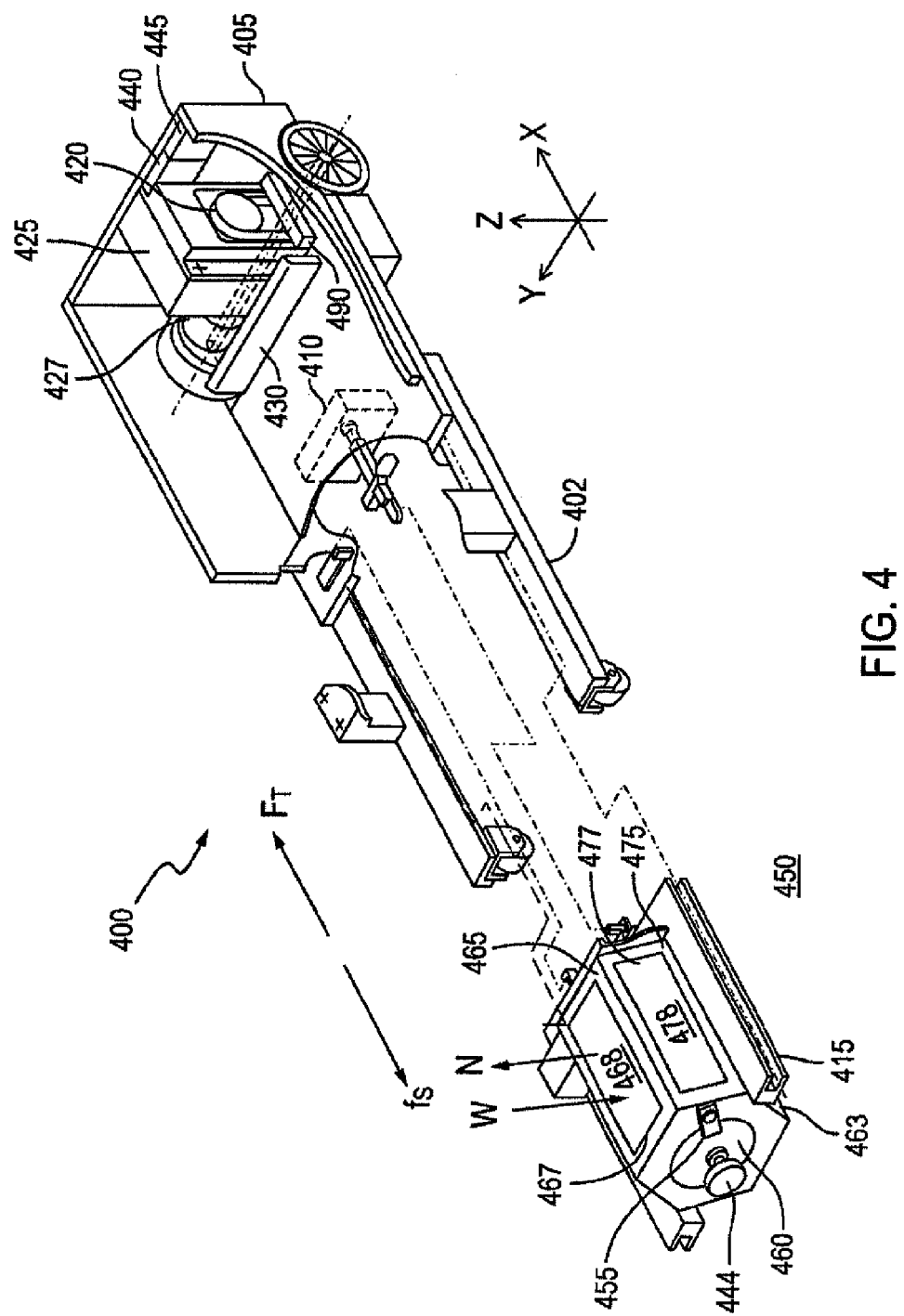
FIG. 4 is an exploded perspective view of an embodiment of an intrinsically calibrated tribometer in FIG. 2, in accordance with the teachings of the present invention.

The embodiment of FIG. 4, depicts a cutaway and extended version of self-propelled tribometer 400, including drive unit 405. Tribometer 400 is similar to tribometer 200 and tribometer 300, with like parts having similar reference numbers. Tribometer 400 also is configured to perform operator-independent self-calibration, greatly reducing or eliminating operator-induced error. Contact sled 415 is depicted as having carrier frame 402 configured to support a six-sided faceted sample carrier 463. Each facet 465, 475 has a workpiece carrier 467, 477, which is configured to releasably retain a respective preselected material sample 468, 478. In general, each facet 465, 475 may have a length greater than its width, and each facet 465, 475 can be aligned with a longitudinal (X) axis of frame 402. Sample carrier 463 may include a central protuberance 444, or knob, to facilitate rotation of sample carrier 463 on frame 415. Such rotation brings preselected material sample 468, 478 into contact with preselected test surface 450. Lock 455 may be provided on sample carrier 463 to prevent inadvertent rotation or misalignment of sample 468, 478 with surface 450. Lock 455 may have locking elements on both frame 402 and carrier sled 415, although other configurations are contemplated. Lock 455 also may provide registration of sample carrier position and, by extension, correspondence of a preselected sample material to a particular test data set. In some embodiments, lock 455 is configured to lock a preselected sample material under test to be substantially parallel to test surface 450. In other embodiments, lock 455 may be configured to permit a selectable degree of off-parallel alignment, where such alignment would be useful in selecting from among a range of possible interfacial test areas between the sample under test and the test surface.

Weight caisson 460 is depicted as being disposed, in whole, in contact sled 415 solely to facilitate exposition. Weight caisson 460 may be disposed in part, or in whole, on one or both of drive unit 405 and contact sled 415. Also, weight caisson 460 is illustrated as being a container having lateral elements and a fixed-weight caisson; however, weight caisson 460 also may be configurable to vary the gravitational force holding preselected material sample 468, 478, for example, in sample carrier 467 or 477 in contact with preselected test surface 450.

Power unit 490 can provide power to one or more elements of drive unit 305, for example, force engine 425 and controller 430. Power unit 490 may be a battery, a fuel cell, or other energy source configured to supply the power of tribometer 400. In certain selected embodiments, power unit 490 may receive at least some power through a lightweight wired electrical link, or a wireless link, such as an electromagnetic induction power transfer source.

Figure 5:
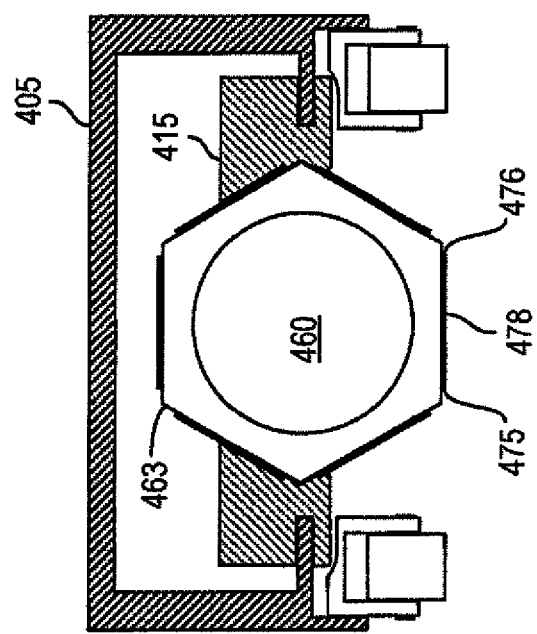
FIG. 5 is a rear view of another embodiment of an intrinsically calibrated tribometer, in accordance with the teachings of the present invention.

FIG. 5 depicts a view of tribometer 400, illustrating an end of a hexagonally-arranged faceted sample carrier 463. Weight caisson 460 is depicted amid the hexagonal sample carrier, upon which facets, such as facet 475, are disposed sample carriers, such as carrier 477, which in turn, retains test sample material 478. Typically, test sample material 478 is held in place on surface 450 while a tractive force is provided by drive unit 405.

Figure 6:
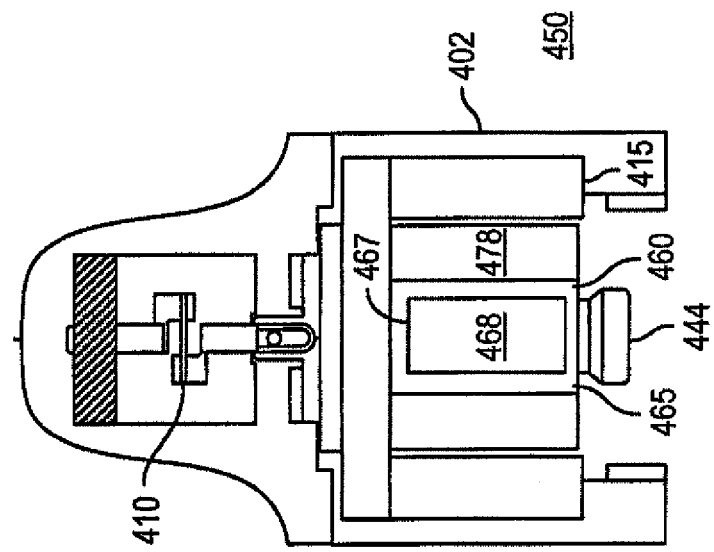
FIG. 6 is a top view of the embodiment of an intrinsically calibrated tribometer shown in FIG. 5, in accordance with the teachings of the present invention.

FIG. 6 illustrates a top view of a contact sled 415 in FIG. 4, which includes carrier frame, and force sensor 410. Again, a hexagonal-faceted version of contact sled 415 is shown, although this configuration is not essential to all embodiments. Weight caisson 460 can be seen as including turning knob 444, which can allow a user to turn sample carrier 463 to a selected test sample, such as sample 468 to be place in contact with test surface 450 (of course, sample 468 would be rotated to be disposed at least partly in contact with test surface 450).

Figure 7:
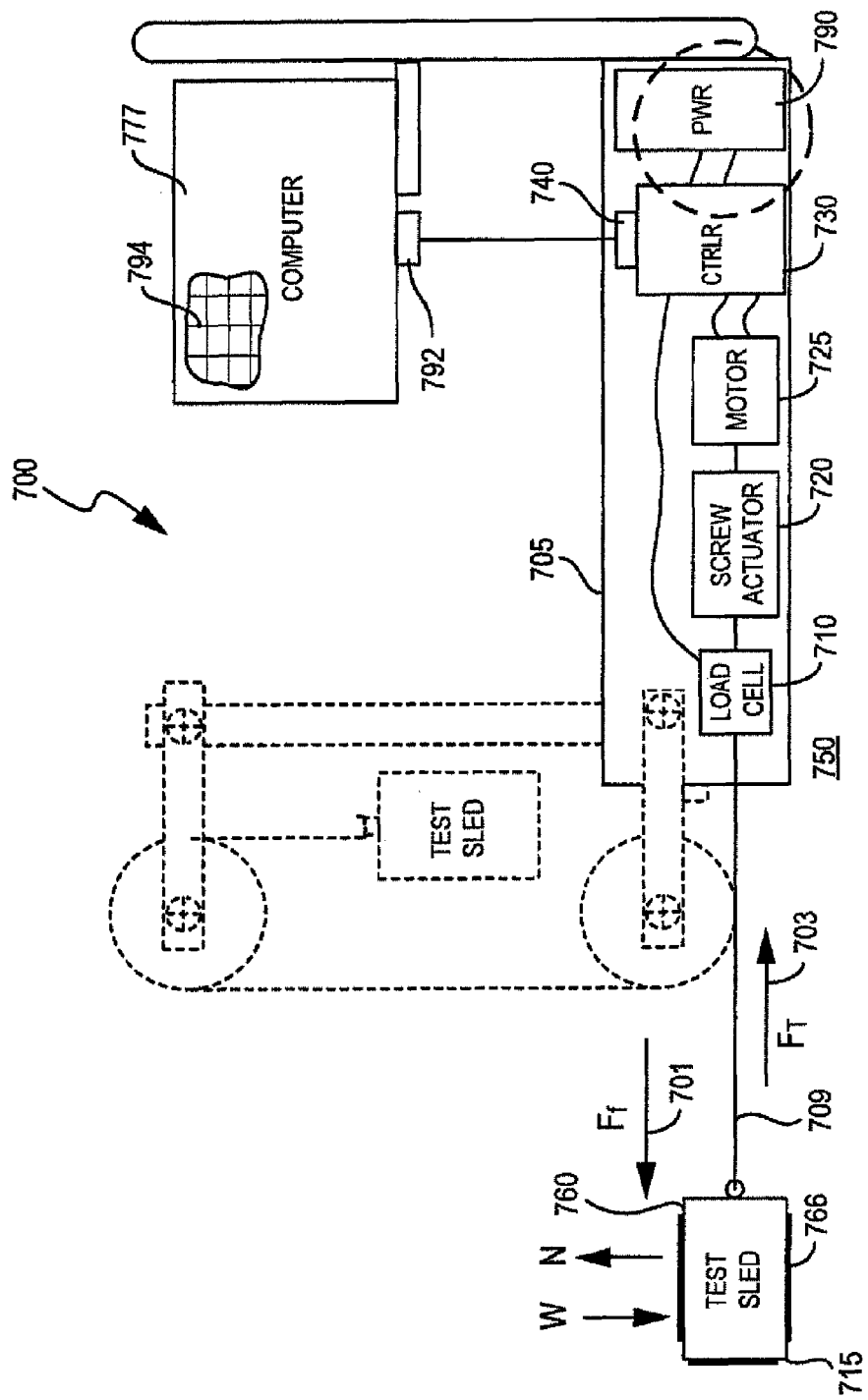
FIG. 7 is a side view illustration of one embodiment of a stationary intrinsically calibrated tribometer, in accordance with the teachings of the present invention.

FIG. 7 is a side view of a stationary embodiment of intrinsically calibrated tribometer 700, in which base 705 can be configured to remain substantially stationary and to apply tractive force 703 to test sled 715 on test surface 750. Tribometer 700 can be similar to tribometer 300, with similar numbers having like meaning. Base 705 generally can be outfitted and configured to include functional units described in FIG. 3, with respect to intrinsically calibrated tribometer 300, without use of self-propulsive or navigational elements. However, positional instrumentation (e.g., GPS or other GIS sensor) may be used, particularly when tribometer 700 is configured for use with plural tribometers. Nevertheless, the operator-independent intrinsically self-calibrating capabilities, and other aforementioned force and coefficient of friction mensuration features, also are included in stationary embodiments. Tribometer 700 may communicate using communications unit 740, as well as by keyboard 792, by display 794, or by both. Tribometer 700 may be coupled to test sled 715 by way of hook 711 and cord 709. Force engine 725 can apply motive force to controllable motive unit 720, which may be a spindle, drum, pulley or other uptake apparatus, and frictional force 701 may be measured by force meter 710, as well as by sensing a state of force engine 725 (e.g., voltage, current, power, or torque).

Test sled 715 includes a multiple carrier test bed 763, which may be configured to hold at least one carrier 766 for a test specimen 768, which may be placed in contact with test surface 750. Test sled 715 may operate similarly to contact sled 415, in that test sled 715 generally may have tractive force, $F_T$, 703 applied by, and be dragged towards, base 705. Test specimen 768 can be any type of material about which friction characteristics may be of interest. One such material includes shoe sole material; another may include shoe heel material, although test specimen and test surfaces are not constrained. Indeed, many surface samples, which may be standardized surface samples, may interchangeably be placed into carrier 766 as a test specimen 768. Typically, tractive force, $F_T$, 703 is opposed by static friction, $f_S$, or by dynamic friction, $f_K$, depending respectively on the kinetic state of the tribometer 700. In general operation, a force 701 resistive to the applied tractive force 703 exists while test sled 715 remains at rest on test surface 750, and can be representative of static friction; on the other hand a force 740 resistive to the applied tractive force exists while test sled 715 is in motion, and can be representative of dynamic friction. Typically, as tractive force 703 is applied to resting test sled 715 on test surface 750, the magnitude of measured static friction 701 increases (similar to the force profile in FIG. 1B), until an inflection point is reached, at which motion occurs in test sled 715. During operation, tractive force may be measured during stationary and moving periods, for example, about 10-20 force measurements, and also may be averaged. Tractive force 703 can be representative of the opposing frictional force. The tractive force can be representative of a measured dynamic coefficient of friction 740, when moving or of a measured static coefficient of friction when tractive force has not yet induced motion in test sled 715. Test sled 715 can be weighted to achieve actual weight "W," and force engine (e.g., motor) 725 in body 705 can pull cord 709 coupled to test sled 715. Controller 730 in base 705 can be a computer, which can cause force measurements "F" to be taken on pulled cord 709, such that the ratio "F/W" may be calculated automatically. Computer 777 can be external but coupled to controller 730. Conveniently, this method can produce calibration values as well as test values. Because of a concern about the impact of "stiction" forces, when motion is incipient, a first value of dynamic friction (or last value of static friction) representative of stiction may be discarded. Similarly, a first averaged value may be discarded to eliminate "stiction" from analysis. However, all values may be retained, if so configured. Computer 702 may be configured to present on a display, measured values and other indicia of operation. Such indicia may include, without limitation, time, date, ambient temperature, atmospheric pressure, ambient light levels, or ambient humidity. Force measurements may be proportional to a voltage used by motor 707 used to create a force to pull cord 709.

In this way, device 700 may be configured to measure both static and dynamic friction. Base 705 can be weighted to remain stationary, be supported by stabilizer 777 or, alternatively, it can be configured to clamp or to adhere to a surface proximate to test surface 750. With these principles in mind, test sled 715 can be outfitted with at least one test specimen 768, which is held in contact with test surface 750. The measured force interactions between test surface 750 and test specimen 768, at rest and during movement, can be characterized by measured static friction and measured dynamic friction, respectively. In some embodiments, test sled 715 may be weighted, for example, with a five pound weight, for example, in weight caisson 760, although other weights may be used. In addition, test sled may be configured to be outfitted with different types of test specimen 768, for example, to test different types of specimen, without limitation, a shoe material, a non-skid surface, or an unquantified specimen to be analyzed. Tribometer 700 may be intrinsically calibrated, as described relative to FIG. 9.

Figure 8:
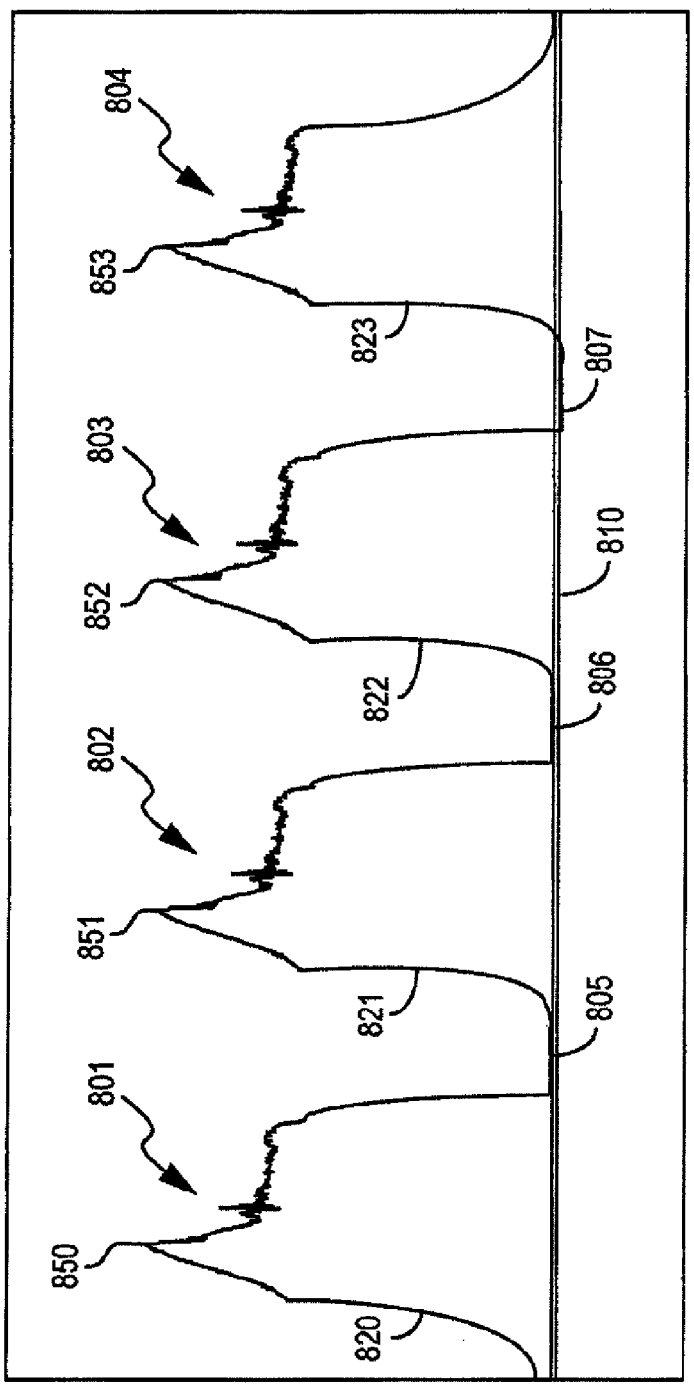
FIG. 8 is an illustration of a multiple epoch test output.

FIG. 8 exemplifies a test period 800 having four (4) test epochs 801-804. The illustrated values of each epoch 801-804 are similar to the values shown in FIG. 1B. However, it is shown that force 810 falls to a minimum 805-807 between epochs 801-804, indicating that the friction mensuration device is stopped and at rest. As tractive force is applied 820-824, the nonce (roughly, the peak value) 850-853 of each test period is indicative of incipient motion in the test piece. Comparable values obtained during each test epoch can be averaged and be subjected to other statistical analyses. Each test epoch 801-804 may be about 5 to 8 seconds in length, and a typical test period 800 may include between about 5 and about 10 epochs, such that a test period 800 may be between about 25 sec. to about 80 sec., a much shorter time than current testing consumes. Longer or shorter test epochs 801-804 or periods 800 may be used but, for many instances between about 5 to about 10 test epochs 801-804 can be sufficient, producing accurate, reliable, and reproducible statistical values.

Figure 9:
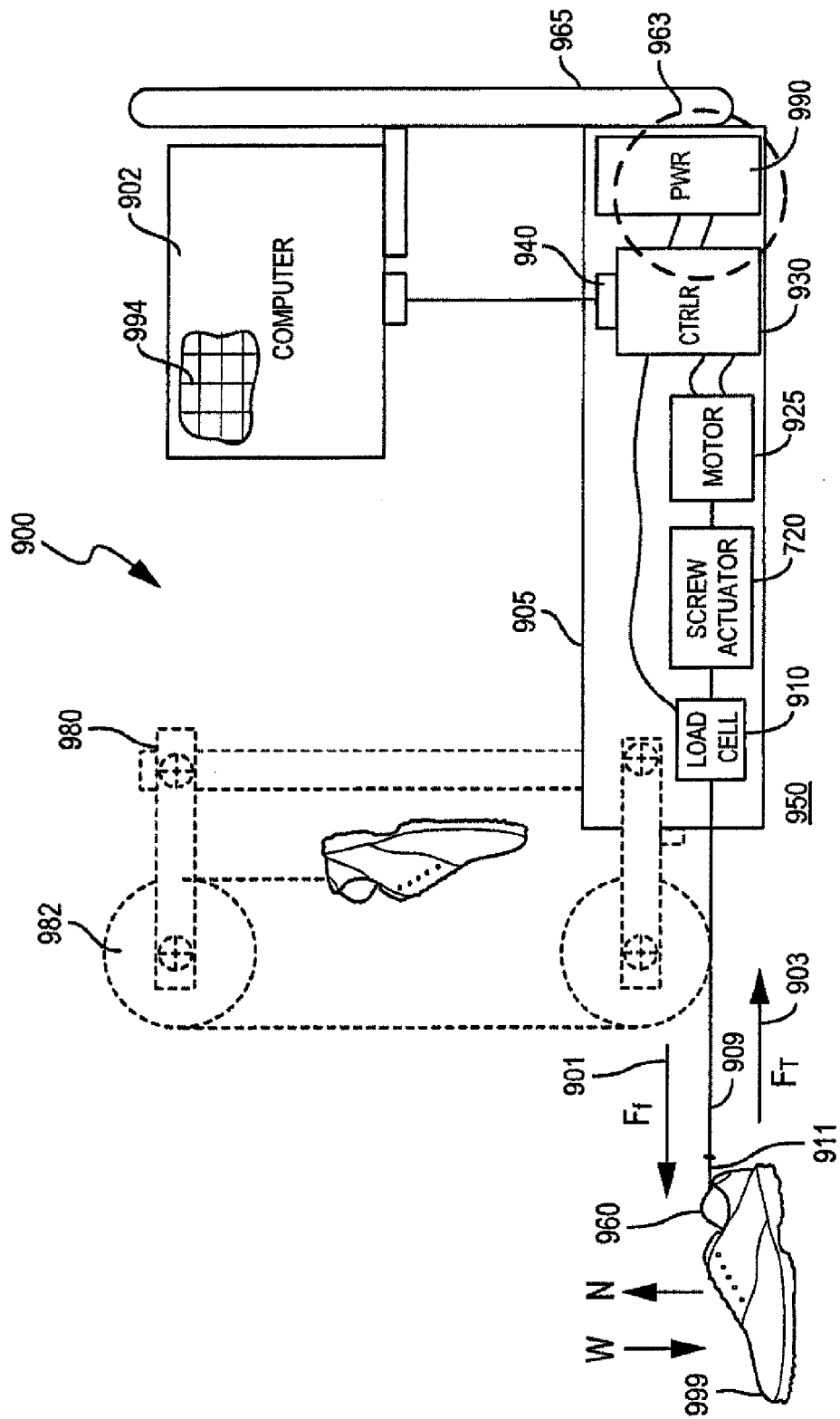
FIG. 9 is a side view illustration of another embodiment of a stationary intrinsically calibrated tribometer, in accordance with the teachings of the present invention.

Turning to FIG. 9, stationary intrinsically calibrated tribometer 900, which can be similar to tribometers 300 and 700, can include base 905, which may be configured to substitute in place of test sled 915, a test article 999, for example, a shoe or other article of study. In the case of a shoe, base 905 may be attach to the test subject shoe 999 by a simple hook 911 and inelastic cord 909 arrangement. Tractive forces then may be applied by base 905 to the test subject shoe 999, as shoe rests on test surface 950. As before, the transition from at-rest to in-motion signifies the transition from static friction to dynamic friction. Where the circumstances of a fall mishap are being investigated forensically, for example, the configuration of base 905 may permit the static and dynamic friction forces of an actual shoe of a fall mishap victim to be tested against the actual surface upon which the victim slipped and fell. Test article 999 may be weighted, for example, using test weight 960, to simulate the victim's weight upon a surface 950 at the moment of simulated fall. Force and weight measurements made by computer 902 may be used to determine static coefficient of friction, dynamic coefficient of friction, or both, of test surface 950, test specimen 999, or both. Controller 930 can operate display 994 to display test indicia and to create a hard-copy (printout) of stored, measured, or calculated data. Controller 930 may be similar to the functional units of FIG. 3, and include flash memory in which to store indicia or data, as well as an USB port to facilitate transfer of data or indicia to, for example, a USB-configured portable memory device. Display 994 may be cooperated with a hard-copy printer (not shown), for example, using a WLAN or WPAN protocol, and may display the actual ramp-up of applied static force, and transition to dynamic force application.

In a prototype device in accordance with the aforementioned principles, eight (8) D-size battery cells 990 may be used by base 905 to provide base weight, to power force engine 925, and to operate computer 930. Instead of a spindle or pulley-type device, force engine (motor) 925 may power a screw rod 920 coupled to force back and forth to achieve the desired force application. The screw rod 920 may have a mechanical auto-stop to prevent over driving. Similarly, force engine 925 can include an electrical, mechanical, or electromechanical stop to prevent over-driving. Also, cord 909 may be threaded through pulley 982 at the apex of stanchion 980, to use controllable motive unit 920 to perform friction force measurements as well as weight measurements. It has been determined that the 8 D-cell batteries may be capable of providing up to one year of intermittent service of device 900, and of providing substantial stabilizing weight to base 905. Base 905 (and base 705 in tribometer 700) may be made of an aluminum block, include an offset pair of wheels 963, and a retractable handle 965 to facilitate movement in transit much like a piece of rolling (pull-along) luggage. The retractable handle may be fitted with a removably attachable shelf 967 to permit handy access to a keyboard, and/or a display and, perhaps, a printer. Intrinsically calibrated tribometer 900 can include one or more handles and securable elements (not shown) by which to reversibly convert device 900 into a single physical unit, convenient for transport and storage. In addition, base 905 may include a stanchion 980 having pulley 982, from which test sled 715 or test device (e.g., shoe) 999 may be suspended. Weight and force calibration also may be determined by lifting the suspended shoe 999 towards the apex of stanchion 980 via pulley 982 such that shoe 999 is free from contact with surface 950 and is suspended from pulley 982. Weight readings may be made and recorded, so that calibration can reflect the actual weight of the shoe or other test piece.

In view of the foregoing, methods for friction measurement are provided, one method including applying an increasing tractive force to a test sled at rest at the beginning of a test epoch or a test period; measuring the tractive force on the test sled at rest on a test surface during a test epoch or a test period; identifying the maximum tractive force applied at incipient motion of the test sled on the test surface during a test epoch or a test period; identifying a nonce of one or more test epochs signifying the transition between the test sled at rest and incipient motion; determining the static coefficient of friction of the test sled relative to the test surface for a test epoch or a test period; measuring the tractive force used to continue motion in the test sled for a test epoch or a test period; stopping the tractive force at the end of a test epoch or a test period; determine the dynamic coefficient of the test sled relative to the test surface for a test epoch or a test period. The method also may include discarding a measurement corresponding to a stiction measurement. The tractive force may be applied by driving a controllable motive element to coupled to a self-propelled device body; by coupling the self-propelled device body to a contact sled against a test surface; by increasing the tractive force until incipient motion of the contact sled occurs; by measuring the tractive force against the contact sled applied at the nonce of incipient motion; by measuring tractive force during contact sled motion during a remainder of a test epoch; by determining the static coefficient of friction of the contact sled with regard to the test surface; and by determining the dynamic coefficient of friction of the contact sled with regard to the test surface.

Intrinsic calibration method may include applying tractive force to a test piece during a calibration period; suspending the test piece off of a weight-bearing surface during the calibration period; and weighing the suspended test piece.

The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals represent similar parts throughout the several views of the drawings, although not every figure may repeat each and every feature that has been shown in another figure in order to not obscure certain features or overwhelm the figure with repetitive indicia. It is understood that the invention is not limited to the specific methodology, devices, apparatuses, materials, applications, etc., described herein, as these may vary. It is also to be understood that the terminology used herein is used for the purpose of describing particular embodiments only, and is not intended to limit the scope of the invention.

What is claimed is:

1. A friction mensuration device, comprising:
   a drive unit having at least one controllable motive member coupled to the drive unit, configured to receive a controllable propulsion force, and configured to apply tractive force to a test piece on a surface responsive to the controllable propulsion force;
   a force engine coupled to the at least one controllable motive member, and configured to apply the controllable propulsion force to the at least one controllable motive member;
   a controller coupled to the force engine, and imposing a propulsion control signal to the force engine, the propulsion control signal actuating the force engine to produce the controllable propulsion force; and
   a force sensor coupled between the drive unit and the test piece, the force sensor producing a force signal responsive to a sensed force between the drive unit and the test piece, wherein a sensed force measurement representative of a stiction force is rejected, and wherein the drive unit is intrinsically calibrated to the Normal force.

2. The friction mensuration device of claim 1, further comprising:
   the test piece having a preselected test material thereon, wherein the test piece is oriented to place the preselected test material in contact with a test surface, and wherein the test piece receives the tractive force wherein the sample carrier translates the tractive force into a test force applied to the preselected material sample, and wherein the test force applied to the preselected material sample is representative of a friction force between the preselected material sample and the surface.

3. The friction mensuration device of claim 1, wherein the drive unit is a self-propelled drive unit coupled to the test piece.

4. The friction mensuration device of claim 1, wherein the drive unit is a stationary drive unit coupled to the test piece.

5. The friction mensuration device of claim 1, wherein the sensed force is a static friction force.

6. The friction mensuration device of claim 1, wherein the sensed force is a dynamic friction force.

7. The friction mensuration device of claim 1, wherein, in response to a received force signal, the controller actuates the force engine to produce a controllable propulsion force on the at least one controllable motive member and, responsive thereto, imposes a friction force imposed between the test surface and the preselected sample material.

8. The friction mensuration device of claim 1, further comprising:
   a mensuration memory coupled to the controller and having memory storage units, the mensuration memory being configured to receive from the controller a plurality of representations of the sense force, and the mensuration memory configured to retain respective ones of the plurality of representations of the sense force.

9. The friction mensuration device of claim 1, wherein the test piece is a contact sled further comprising:
   a carrier having facets, wherein each of the facets includes a sample carrier thereon, each sample carrier being disposed to releasably retain a respective preselected material sample, and wherein the carrier can be disposed to position one of the preselected test materials in contact with the surface.

10. The friction mensuration device of claim 1, further comprising: the force engine applies the tractive force during a first portion of a test epoch, corresponding to the static coefficient of friction.

11. The friction mensuration device of claim 1, wherein one of the preselected sample materials is a control sample material.

12. The friction mensuration device of claim 11, wherein the control sample material is a piece of footwear.

13. The friction mensuration device of claim 11, wherein the control sample material is a resin rubber constituent of a preselected rubber soling material.

14. A method of friction mensuration, comprising:
   applying an increasing tractive force to a test piece at rest on a test surface at the beginning of a test epoch;
   measuring the tractive force on the test piece at rest on a test surface during the test epoch;
   identifying the maximum tractive force applied at incipient motion of the test piece on the test surface during the test epoch;
   identifying a nonce of the test epoch signifying the transition between the test piece at rest and incipient motion;
   determining the static coefficient of friction of the test piece relative to the test surface for the test epoch, wherein a sensed force measurement representative of a stiction force is rejected; and
   measuring the tractive force used to continue motion in the test sled for the test epoch.

15. The method of friction mensuration of claim 14, further comprising:

creating a test period from a plurality of sequential test epochs.

16. The method of friction mensuration of claim 15, further comprising:
   stopping the test piece between selected test epochs in the test period.

17. The method of friction mensuration of claim 14, further comprising:
   applying tractive force to the test piece during a calibration period;
   suspending the test piece separated from the test surface during the calibration period; and
   weighing the suspended test piece, wherein the weighing is a constituent of intrinsically calibrating a friction mensuration device.

18. The method of friction mensuration of claim 14, further comprising:
   continuing the tractive force during the test epoch; stopping the tractive force at the end of a test epoch;
   determining the static coefficient of friction of the test piece relative to the test surface; and
   determining the dynamic coefficient of friction of the test piece relative to the test surface.

19. The method of friction mensuration of claim 14, further comprising:
   applying tractive force to the test piece during a calibration period;
   suspending the test piece separated from the test surface during the calibration period; and
   weighing the suspended test piece, wherein the weighing is a constituent of intrinsically calibrating a friction mensuration device.

20. The method of friction mensuration of claim 19, further comprising:
   applying tractive force to the test piece during a calibration period;
   suspending the test piece separated from the test surface during the calibration period; and
   weighing the suspended test piece, wherein the weighing is a constituent of intrinsically calibrating a friction mensuration device.

* * * * *